United States Patent
Tekulve

(10) Patent No.: US 9,522,258 B2
(45) Date of Patent: Dec. 20, 2016

(54) CLOT REMOVAL SYSTEM AND METHOD

(71) Applicant: Kurt Tekulve, Ellettsville, IN (US)

(72) Inventor: Kurt Tekulve, Ellettsville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 894 days.

(21) Appl. No.: 13/742,621

(22) Filed: Jan. 16, 2013

(65) Prior Publication Data

US 2013/0226146 A1 Aug. 29, 2013

Related U.S. Application Data

(60) Provisional application No. 61/602,696, filed on Feb. 24, 2012.

(51) Int. Cl.
| | |
|---|---|
| *A61M 5/315* | (2006.01) |
| *A61M 25/10* | (2013.01) |
| *A61M 25/09* | (2006.01) |
| *A61B 17/3207* | (2006.01) |
| *A61B 17/22* | (2006.01) |
| *A61B 17/00* | (2006.01) |
| *A61B 17/221* | (2006.01) |

(52) U.S. Cl.
CPC .... *A61M 25/104* (2013.01); *A61B 17/320725* (2013.01); *A61M 25/09* (2013.01); *A61B 17/22031* (2013.01); *A61B 2017/00867* (2013.01); *A61B 2017/2215* (2013.01); *A61B 2017/22084* (2013.01)

(58) Field of Classification Search
CPC .......... G06F 17/30569; G06F 17/3089; A61M 25/104;A61M 25/09; A61B 17/320725; A61B 17/22031; A61B 2017/2215; A61B 2017/22084; A61B 2017/00867
USPC .................................... 604/509–510, 101.01
See application file for complete search history.

(56) References Cited

U.S. PATENT DOCUMENTS

| | | | |
|---|---|---|---|
| 5,030,201 A | 7/1991 | Palestrant | |
| 5,501,654 A | 3/1996 | Failla et al. | |
| 5,766,191 A | 6/1998 | Trerotola | |
| 5,833,644 A * | 11/1998 | Zadno-Azizi | A61B 17/22 604/101.05 |

(Continued)

FOREIGN PATENT DOCUMENTS

WO 97/26832 7/1997

*Primary Examiner* — Theodore Stigell
*Assistant Examiner* — Amber Stiles
(74) *Attorney, Agent, or Firm* — Liell + McNeil

(57) ABSTRACT

A clot removal system includes an elongated tubular sheath and an elongated tubular catheter received within the sheath. A distal segment of the catheter is split into a plurality of catheter wall segments, with each wall segment having a pre-shaped curved configuration. Each wall segment defines at least one scraping edge and has a distal tip that is less stiff than a remaining portion of the wall segment. The clot removal system has a transport configuration in which the distal segment of the catheter is axially aligned with a distal segment of the sheath and the wall segments are urged against the pre-shaped curved configuration by the sheath. The clot removal system also has a deployed configuration in which the distal segment of the catheter is advanced distally beyond the distal segment of the sheath and the wall segments conform to the pre-shaped curved configuration.

17 Claims, 4 Drawing Sheets

(56) References Cited

U.S. PATENT DOCUMENTS

| | | |
|---|---|---|
| 6,758,836 B2 | 7/2004 | Zawacki |
| 6,780,175 B1 * | 8/2004 | Sachdeva ............ A61B 1/00082 |
| | | 604/105 |
| 6,796,989 B2 | 9/2004 | Uflacker |
| 7,303,531 B2 | 12/2007 | Lee et al. |
| 7,645,290 B2 | 1/2010 | Lucas |
| 2003/0093105 A1 * | 5/2003 | Huffmaster ...... A61B 17/12113 |
| | | 606/192 |
| 2006/0253145 A1 | 11/2006 | Lucas |
| 2008/0021383 A1 * | 1/2008 | Pierpont ............. A61M 25/104 |
| | | 604/101.01 |
| 2009/0254038 A1 | 10/2009 | Lapeyre |
| 2010/0324576 A1 | 12/2010 | Pintor et al. |

\* cited by examiner

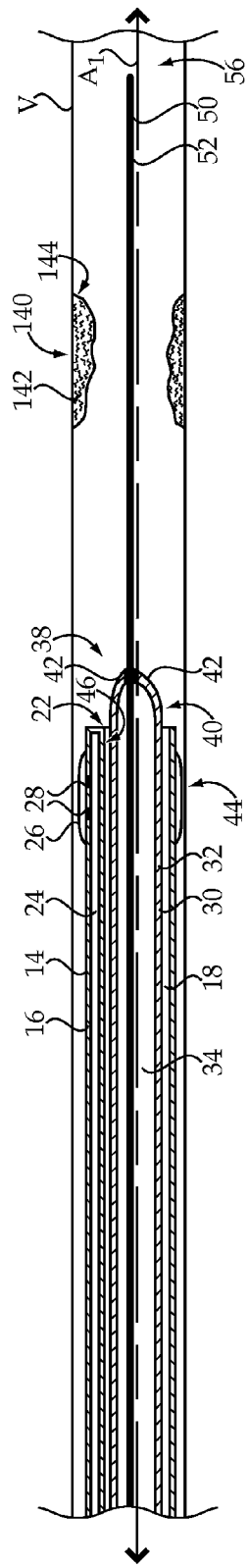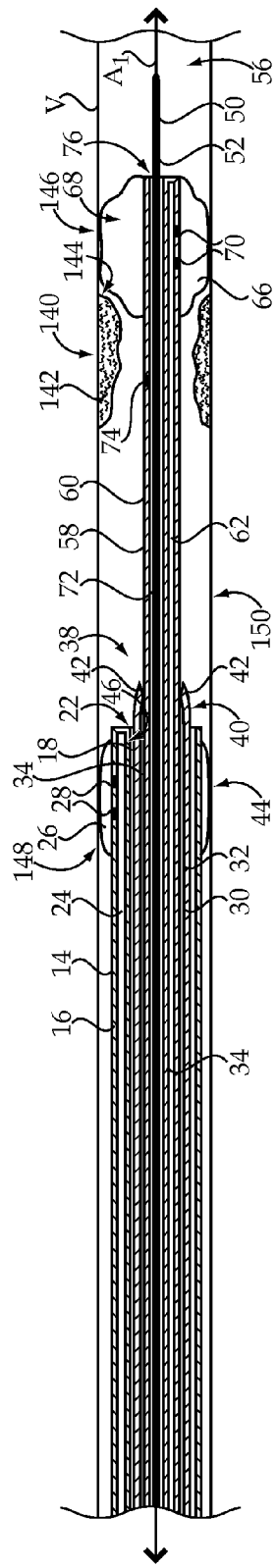

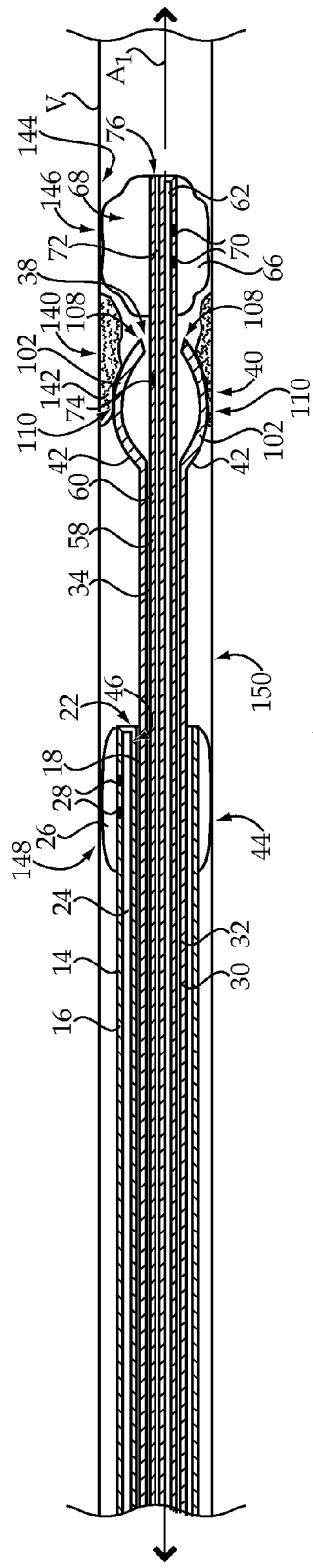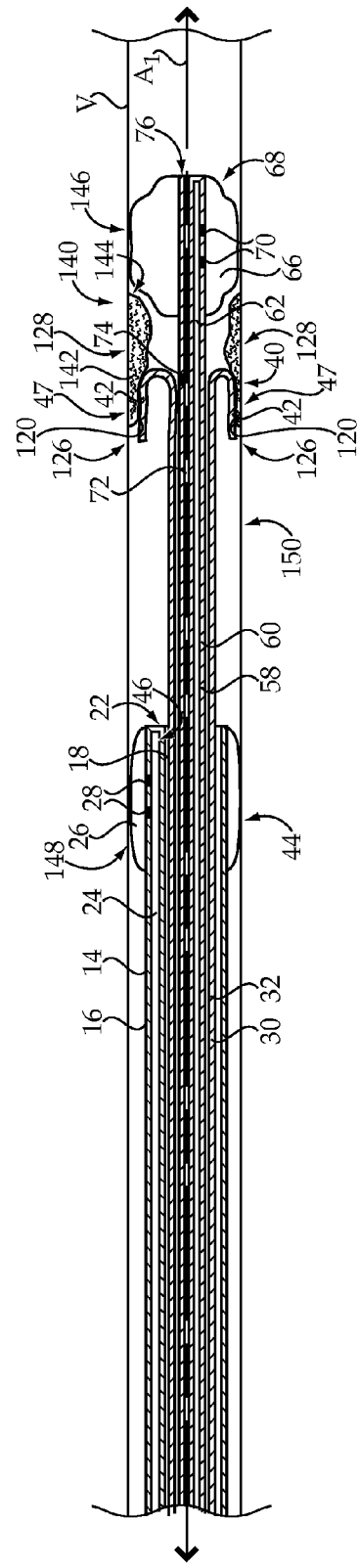

CLOT REMOVAL SYSTEM AND METHOD

RELATION TO OTHER PATENT APPLICATION

This application claims priority to provisional patent application 61/602,696, filed Feb. 24, 2012, with the same title.

TECHNICAL FIELD

The present disclosure relates generally to a clot removal system having an elongated tubular catheter received within an elongated tubular sheath, and more particularly to a catheter that is distally split into a plurality of catheter wall segments having pre-shaped curved configurations.

BACKGROUND

Thrombosis is the formation of a thrombus, or blood clot, within the vascular system of a patient. A blood clot typically occurs when blood hardens from a liquid to a solid. When attached to vessel walls, blood clots, and other substances, such as plaque or fat, may reduce or block blood flow downstream from the clot. This partially or completely blocked blood flow may prevent normal blood flow and oxygen from reaching certain tissues and, thus, may result in damage to the tissues. If a clot becomes dislodged from the vessel walls it may travel to other portions of the vascular system, where it may ultimately occlude critical blood flow. Regardless of the particular location of the clot within the vascular system, clots consisting of blood or other substances, if left untreated, may cause serious damage and, in some cases, may become life threatening.

A wide variety of invasive and non-invasive techniques are available for breaking up and/or removing clots within the vascular system. For example, some techniques include the use of pharmacological agents, also referred to as thrombolytic agents, to help dissolve the clots. Other techniques may include the use of mechanical agitation to dislodge clots from walls of the vascular system. For example, a device described in U.S. Pat. No. 7,645,290 to Lucas includes a catheter having tines that are allowed to expand radially, such as about living hinges, upon the proximal displacement of a sheath. While rotation and/or axial movement of the tined catheter may break up the clot into smaller pieces, the distal tips of the finger-like tines may potentially damage the vessel walls, particularly during reciprocating axial movement. A number of additional risks are associated with clot removal procedures, including risks associated with the use of thrombolytic agents and risks associated with the migration of dislodged portions of the clot. Further, there is a continuing need for clot removal systems that minimize these risks and more efficiently remove clots.

The present disclosure is directed toward one or more of the problems set forth above.

SUMMARY OF THE DISCLOSURE

In one aspect, a clot removal system includes an elongated tubular sheath and an elongated tubular catheter received within the sheath. A distal segment of the catheter is split into a plurality of catheter wall segments, with each wall segment having a pre-shaped curved configuration. Each wall segment defines at least one scraping edge and has a distal tip that is less stiff than a remaining portion of the wall segment. The clot removal system has a transport configuration in which the distal segment of the catheter is axially aligned with a distal segment of the sheath and the wall segments are urged against the pre-shaped curved configuration by the sheath. The clot removal system also has a deployed configuration in which the distal segment of the catheter is advanced distally beyond the distal segment of the sheath and the wall segments conform to the pre-shaped curved configuration.

In another aspect, a method for removing a clot from a patient vessel includes the use of a clot removal system comprising an elongated tubular catheter received within an elongated tubular sheath. A distal segment of the catheter is split into a plurality of catheter wall segments, with each wall segment having a pre-shaped curved configuration. The method includes advancing the clot removal system through the patient vessel in a transport configuration toward the clot. In the transport configuration, the distal segment of the catheter is axially aligned with a distal segment of the sheath and the wall segments are urged against the pre-shaped curved configuration by a lumen wall of the sheath. The clot removal system is then moved from the transport configuration to a deployed configuration. In the deployed configuration, the distal segment of the catheter is advanced distally beyond the distal segment of the sheath and the wall segments conform to the pre-shaped curved configuration. A portion of the clot is dislodged from the vessel wall using a scraping edge of at least one of the wall segments.

BRIEF DESCRIPTION OF THE DRAWINGS

FIG. 4 is a side diagrammatic view of a vascular structure of a patient at one stage of a clot removal procedure using the clot removal system of FIG. 1;

FIG. 5 is a side diagrammatic view of the vascular structure of a patient at another stage of a clot removal procedure using the clot removal system of FIG. 1;

FIG. 6 is a side diagrammatic view of the vascular structure of a patient at another stage of a clot removal procedure using the clot removal system of FIG. 1 and, in particular, using a catheter having the pre-shaped curved configuration of FIG. 2; and FIG. 7 is a side diagrammatic view of the vascular structure of a patient at another stage of a clot removal procedure using the clot removal system of FIG. 1 and, in particular, using a catheter having the pre-shaped curved configuration of FIG. 3.

DETAILED DESCRIPTION

Figure 1:
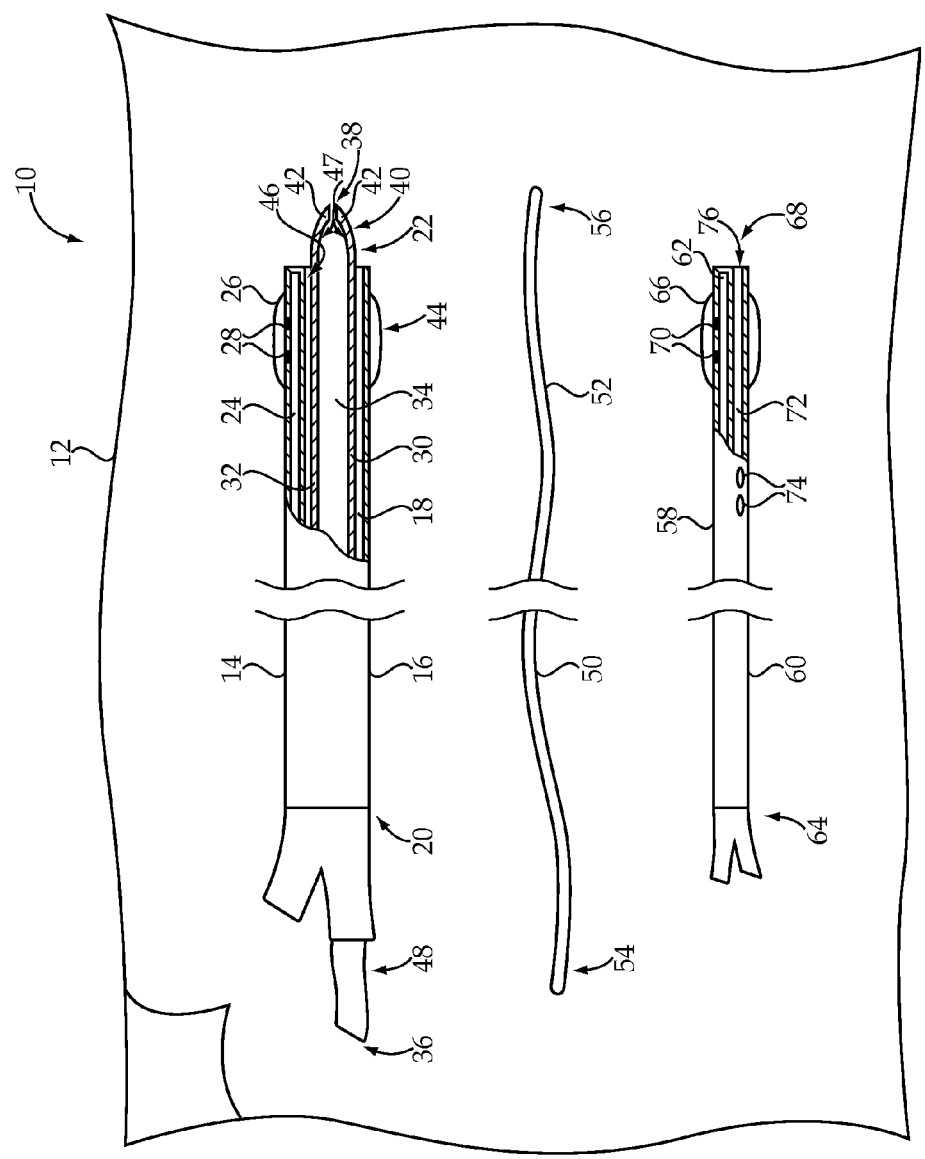
FIG. 1 is a partially sectioned side diagrammatic view of a clot removal system, according to one embodiment of the present disclosure.

Referring to FIG. 1, there is shown a clot removal system 10 according to one embodiment of the present disclosure. The clot removal system 10 may include a number of components, which may be provided within a sterile, tear open package 12, as is known in the art. In performing a clot removal procedure on a patient, some or all of the components of the clot removal system 10 may be used, depending upon the specifics of the procedure to be performed. As should be appreciated, however, the components shown in FIG. 1 might be separately packaged and/or the clot removal system 10 might also include components in addition to those shown, including components routinely used in percutaneous vascular procedures.

The clot removal system 10 generally includes an elongated tubular sheath 14. The sheath 14 may include an elongated tubular body 16 defining at least one device lumen 18 extending from an open proximal end 20 to an open distal end 22 of the elongated tubular body 16. The elongated tubular body 16 may be made from any common medical tube material, such as, for example, polytetrafluoroethylene (PTFE), high density polyethylene (HDPE), nylon, polyetheretherketone (PEEK), or any vinyl, plastic, rubber, or silicone, and may exhibit both stiffness, or firmness, and flexibility. Materials as well as dimensions may vary depending on the particular application. In the present disclosure, "proximal" will be used to refer to the end of a component or feature that is closest to a clinician, while "distal" is used to refer to a component or feature that is farthest away from the clinician. Such meanings are consistent with conventional use of the terms and, as such, should be understood by those skilled in the art.

According to some embodiments, the sheath 14 may also have an inflation lumen 24 extending from the open proximal end 20 to an inflatable balloon 26 mounted on the distal end 22 of the sheath 14. The inflation lumen 24 may be in fluid communication with the interior of the inflatable balloon 26 via openings 28 through the elongated tubular body 16. Thus, as should be appreciated, a fluid source may be used to inflate the inflatable balloon 26 via the inflation lumen 24 and openings 28. When inflated, or deployed, the inflatable balloon 26 may function as a barrier during a clot removal procedure, as will be discussed below. Alternatively, however, the sheath 14 may include only the device lumen 18, or may include more than two lumens, depending on the particular application. As should be appreciated, the sheath 14 may include additional devices or components, including ports, clamps, and connecting devices, as necessary to perform the clot removal procedure described herein.

According to the exemplary embodiment, an elongated tubular catheter 30 is received within the device lumen 18 of the sheath 14. The catheter 30 may also include an elongated tubular body 32 defining at least one lumen 34 extending from an open proximal end 36 to an open distal end 38 of the elongated tubular body 32. Similar to the sheath 14, the elongated tubular body 32 may also be made from any common medical tube material, such as, for example, PTFE, HDPE, nylon, PEEK, or any vinyl, plastic, rubber, or silicone, and may exhibit both stiffness, or firmness, and flexibility. Materials as well as dimensions may also vary depending on specific requirements of the clot removal procedure being performed. However, according to all embodiments, the catheter 30 and sheath 14 are sized such that the catheter 30 may be telescopically received within, and movable through, the sheath 14.

A distal segment 40 of the catheter 30 is split into a plurality of catheter wall segments 42, which will be discussed below in greater detail. The catheter 30 and sheath 14 components of the clot removal system 10 are shown in FIG. 1 in a transport configuration in which the distal segment 40 of the catheter 30, or at least a portion thereof, is axially aligned with, or telescopically disposed within, a distal segment 44 of the sheath 14. Further, according to the transport configuration, the wall segments 42 are each urged against a pre-shaped curved configuration, which will be described below, by a lumen wall 46 of the sheath 14. Thus, the distal segment 40 of the catheter 30, including the wall segments 42, is sufficiently disposed within the distal segment 44 of the sheath 14 such that the sheath 14 restricts the wall segments 42 from conforming to the pre-shaped curved configurations. According to all embodiments, an inner surface 47 of each wall segment 42 faces radially inward in the transport configuration.

As shown, the distal segment 40 of the catheter 30 may be distally tapered, in the transport configuration, allowing the catheter 30 to function as a dilator during advancement of the sheath 14 and catheter 30 configuration. Specifically, during advancement of the catheter 30 and sheath 14, a portion of the distal segment 40 of the catheter 30 may protrude distally beyond the open distal end 22 of the sheath 14. This tapered segment may occupy space between a wire guide and the sheath 14 and may ease advancement of the clot removal system 10. According to some embodiments, the distal segment 44 of the sheath 14 may be distally tapered, or neither or both of the distal segments 40 and 44 may be tapered.

According to most embodiments, a proximal segment 48 of the catheter 30 extends proximally from the open proximal end 20 of the sheath 14 to allow manipulation of the catheter 30 relative to the sheath 14 by a clinician. Specifically, as will become more clear below, a clinician may grasp the proximal end 20 of the sheath 14 and/or proximal segment 48 of the catheter 30 to move one of the sheath 14 and catheter 30 relative to the other and achieve various configurations of the clot removal system 10, including the transport configuration. Further, as will become more apparent below, a clinician may wish to grasp the proximal segment 48 of the catheter to rotate and/or axially reciprocate the distal segment 40 of the catheter 30 during a clot removal procedure. Known tools or devices may be added to the proximal segment 48 of the catheter 30 and/or the proximal end 20 of the sheath 14 to assist in such manipulation.

The clot removal system 10 may also include at least one wire guide 50, which is a device commonly used in vascular procedures to introduce a wide variety of medical devices into the vascular system. Generally speaking, the wire guide 50 includes an elongate flexible body 52 extending from a proximal end 54 to a distal end 56. Since wire guides are known, wire guide 50 will not be discussed herein in greater detail. However, it should be noted that wire guide 50 may be made from any of a number of known materials commonly used to manufacture medical devices and may include any of a variety of known configurations. For example, some wire guides include an elongate core element with one or more tapered sections near a distal end thereof. A flexible helical coil may be disposed about at least a distal portion, such as a tapered portion, of the core element. According to all embodiments, the dimensions and materials of the wire guide 50 may be selected to enhance advancement through the vasculature of the patient, while maintaining an outer diameter that facilitates advancement of the other components of the clot removal system 10 over the wire guide 50.

An infusion catheter 58 may also be provided with the clot removal system 10. The infusion catheter 58 may be similar in construction to the sheath 14 and/or catheter 30 and may include an elongated tubular body 60 defining at least one lumen. According to a specific example, the infusion catheter 58 may include an inflation lumen 62 extending from an open proximal end 64 to an inflatable balloon 66 mounted on a distal end 68 of the infusion catheter 58. The inflation lumen 62 may be in fluid communication with the interior of the inflatable balloon 66 via openings 70 through the elongated tubular body 60. Thus, as should be appreciated, a fluid source may be used to inflate the inflatable balloon 66 via the inflation lumen 62 and openings 70. When inflated, or deployed, the inflatable balloon 66 may function as a barrier, as will be discussed below. The infusion catheter 58 may also include an infusion lumen 72, which is separate from the inflation lumen 62 and may extend from the open proximal end 64 to one or more infusion ports 74 or openings 76 located at or near the distal end 68 of the infusion catheter 58. The infusion lumen 72, as will be discussed below, may be used for deploying thrombolytic agents of the clot removal system 10. The infusion catheter 58 or, more particularly, the infusion lumen 72 may be sized to advance over the wire guide 50. Further, an outer diameter of the infusion catheter 58 may be sized to advance through the catheter 30.

Figure 2:
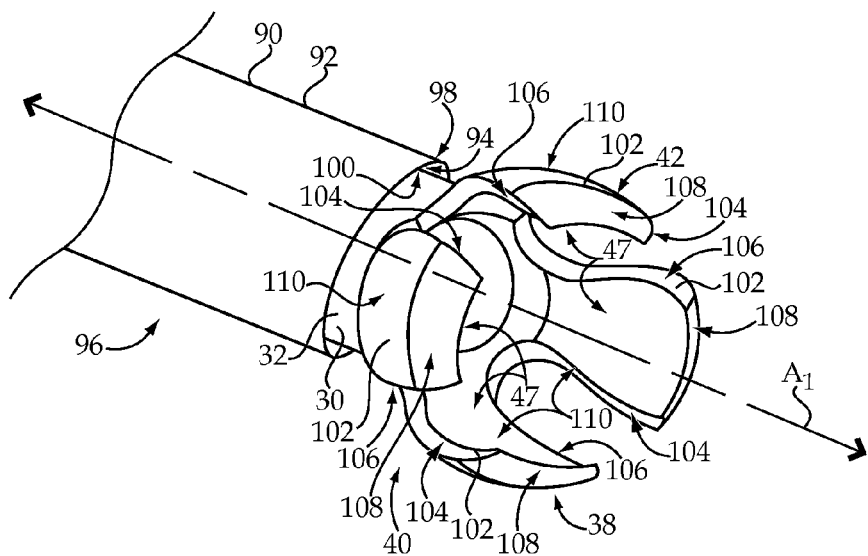
FIG. 2 is a perspective view of the catheter of the clot removal system of FIG. 1, shown in a deployed configuration relative to an exemplary sheath and having a first exemplary pre-shaped curved configuration.

Turning now to FIG. 2, the catheter wall segments 42 and, more particularly, the pre-shaped curved configurations will be discussed in greater detail. For ease of explanation, the catheter 30 of the clot removal system 10 is shown received within a standard sheath 90 having an elongated tubular body 92 defining a single lumen 94. The catheter 30 and sheath 90 are shown in a deployed configuration, in which the distal segment 40 of the catheter 30 has been advanced distally beyond a distal segment 96 of the sheath 90 and through an open distal end 98 of the sheath 90. Specifically, one of the sheath 90 and catheter 30 are moved relative to a longitudinal axis $A_1$ such that the catheter segments 42 are no longer urged against the pre-shaped curved configurations by a lumen wall 100 of the sheath 90. Thus, according to the deployed configuration, the catheter wall segments 42 are able to conform to the pre-shaped curved configurations.

According to a first exemplary pre-shaped curved configuration, the catheter wall segments 42 may include four leaflets 102 that radially expand and assume substantially concave, or scoop-like, shapes. Each of the leaflets 102 has a first directional cutting edge 104 and a second directional cutting edge 106. For example, the first directional cutting edges 104 may be configured to engage a clot when the catheter 30 is rotated in a first direction about the longitudinal axis $A_1$, while the second directional cutting edges 106 may be configured to engage the clot when the catheter 30 is rotated in a second, or opposite, direction about the longitudinal axis $A_1$. As used herein, the cutting edges 104 and 106 may include edges that are shaped, dimensioned, and configured to scrape, cut, or otherwise dislodge or break up the clot. For example, the angle of the cutting edges 104 and 106 relative to the longitudinal axis $A_1$, as well as the thickness and length of the edges 104 and 106, must all be selected to provide desired clot disruption capabilities.

Each of the leaflets 102 also has a distal tip 108 that is less stiff than a remaining portion 110 of the leaflet 102. Specifically, the remaining portion 110, or a majority of, each leaflet 102 should be sufficiently stiff in order to break up or dislodge the clot, while the distal tip 108, at least at the edges thereof, is relatively soft and/or flexible to facilitate atraumatic movement of the catheter 30. For example, during advancement of the catheter 30 and sheath 14 to a clot location and during rotation and/or axial reciprocation of the catheter 30 relative to the clot, the relatively soft distal tips 108, or edges, may reduce the likelihood of puncturing or tearing the vessel walls during a clot removal procedure.

As stated above, a majority of the catheter 30 may be made from any common medical tube material, such as, for example, PTFE, HDPE, nylon, PEEK, or any vinyl, plastic, rubber, or silicone, and may exhibit both stiffness, or firmness, and flexibility. The distal segment 40 or, more specifically, the wall segments 42 of the catheter 30 may be made from or may be embedded with a shape memory alloy, such as, for example, nitinol. Other materials exhibiting shape memory and/or superelasticity properties may also be used to form the desired pre-shaped curved configurations of the wall segments 42. Such materials must be capable of deforming during the transport configuration, as described above, and later resuming the pre-shaped curved configurations during the deployed configuration. The soft distal tips 108 may be made from a relatively soft and flexible medical tube material and, further, may be free from the shape memory alloy embedded within or comprising the remaining portions 110 of the wall segments 42. For example, the distal tips 108, or at least the edges thereof, may be made from or may include a coating of a polyurethane, nylon, or other relatively soft material, but may comprise a base of stiffer material to provide desired support.

Figure 3:
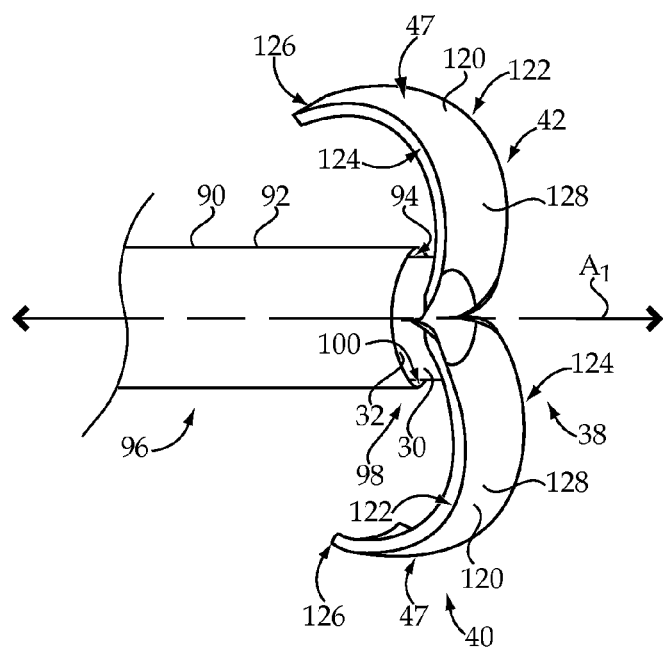
FIG. 3 is a perspective view of the catheter of the clot removal system of FIG. 1, shown in a deployed configuration relative to an exemplary sheath and having a second exemplary pre-shaped curved configuration.

Turning now to FIG. 3, a second exemplary pre-shaped curved configuration is shown. Specifically, in the deployed configuration, the catheter wall segments 42 may include two leaflets 120 that are curved back over a portion of the catheter 30 and, in some cases, the sheath 90. As shown, the inner surface 47 of each wall segment 42, which faced radially inward in the transport configuration of FIG. 1, may now face radially outward in the deployed configuration. Both of the leaflets 120 have first directional cutting edges 122 and second directional cutting edges 124, such that the first directional cutting edges 122 may be configured to engage the clot when the catheter 30 is rotated in a first direction, while the second directional cutting edges 124 may be configured to engage the clot when the catheter 30 is rotated in a second direction.

The leaflets 120 may similar to the leaflets 102 of FIG. 2 in materials and/or configurations. Specifically, for example, the cutting edges 122 and 124 may be shaped, dimensioned, and configured to scrape, cut, or otherwise dislodge or break up the clot. Distal tips 126 of the leaflets 120 are also less stiff than remaining portions 128 of the leaflets 120. For example, the majority 128 of the leaflets 120 may be made from or may be embedded with a shape memory alloy, such as, for example, nitinol, while the soft distal tips 126 may be made from a relatively soft and flexible medical tube material. Further, the distal tips 126 may be free from the shape memory alloy embedded within or comprising the remaining portions 128 of the leaflets 120. Again, it may be desirable for the majority 128 of each leaflet 120, including cutting edges 122 and 124 to be sufficiently stiff in order to break up or dislodge the clot, while the distal tip 126 is relatively soft and/or flexible to facilitate atraumatic movement of the catheter 30 during a clot removal procedure, including movement of the catheter 30 into the deployed configuration.

The clot removal system 10 may also include a thrombolytic agent, or pharmacological agent, that breaks down clots. Exemplary thrombolytic agents may include streptokinase, urokinase, tissue plasminogen activators (tPA), and other similar agents. The thrombolytic agent may be used in conjunction with other components of the clot removal system 10 to break down and remove a clot within the vascular system of a patient. An exemplary clot removal procedure will be discussed in detail below.

INDUSTRIAL APPLICABILITY

The present disclosure is generally applicable to medical devices for use in percutaneous vascular procedures, or other procedures involving cavities, ducts, or canals of a patient. More specifically, the present disclosure is applicable to systems and methods for removing clots, which may include, blood clots, plaque, fat, and other clot forming materials, from the vascular system of a patient. Yet further, the present disclosure may be specifically applicable to clot removal systems including mechanical breakdown of clots.

Referring to FIGS. 4-7, a percutaneous vascular procedure using the clot removal system 10 of FIG. 1 will be described with reference to a vascular structure V of a patient. Although not shown, a clinician may position a needle, or introducer, through the skin of a patient to gain access to the vascular structure V. At a first stage of the procedure, and as shown in FIG. 4, a clinician may insert the wire guide 50 through a tube of the introducer and into the vascular structure V. The wire guide 50 may be placed across a thrombosed section 140 of the vascular structure V. More specifically, the wire guide 50 may be placed across a clot 142 attached to walls 144 of the vascular structure V.

At this stage, or later in the procedure, the sheath 14 and catheter 30 may together be introduced over the wire guide 50. As shown, the sheath 14 and catheter 30 may be advanced through the vascular structure V in the transport configuration. Specifically, according to the transport configuration, the distal segment 40 of the catheter 30 is, at least partially, axially aligned with the distal segment 44 of the sheath 14, and the catheter wall segments 42 are urged against the pre-shaped configuration by the lumen wall 46 of the sheath 14. The tapered distal segment 40 of the catheter 30, which may distally protrude from the sheath 14, may allow the catheter 30 to function as a dilator and may gradually expand the vascular structure V during advancement. Specifically, the tapered distal segment 40 may occupy the space between the wire guide 50 and the sheath 14 and may provide a smoother advancement of the clot removal system components, with less risk of damaging the vessel walls 144.

Turning now to FIG. 5, the infusion catheter 58 or, more particularly, the infusion lumen 72, may be advanced over the wire guide 50 and through the catheter 30. The infusion catheter 58 may be advanced distally beyond the clot 142, such that the inflatable balloon 66 may be distally deployed relative to the clot 142 to function as a first barrier 146. Specifically, the inflatable balloon 66 of the infusion catheter 58 may be inflated using the inflation lumen 62, which is in fluid communication with a fluid source. The inflatable balloon 66, when inflated or deployed, may function as the first barrier 146. Similarly, the inflatable balloon 26 of the sheath 14 may be proximally deployed relative to the clot 142 to function as a second barrier 148. Specifically, the inflatable balloon 26 of the sheath 14 may be inflated using the inflation lumen 24, which is in fluid communication with a fluid source. The inflatable balloon 26, when inflated or deployed, may function as the second barrier 148.

The barriers 146 and 148 may define an isolated segment 150 within the vascular structure V. A thrombolytic agent, such as, for example, streptokinase, urokinase, or tPA, may be delivered into the isolated segment 150 through the infusion lumen 72 of the infusion catheter 58. The thrombolytic agent may be used to dissolve the clot 142. The first and second barriers 146 and 148 function to reduce the amount of thrombolytic agent that may travel past the barriers 146 and 148 and beyond the isolated segment 150 into other areas of the vascular system. It should be appreciated that the thrombolytic agent may cause unwanted bleeding in other areas of the vascular system and, thus, it may be desirable to restrict exposure of the thrombolytic agent to the isolated segment 150. Isolating the thrombolytic agent to precisely where it is needed may also allow a minimal amount of the thrombolytic agent to be used and, thus, may reduce costs of the procedure.

After the sheath 14, catheter 30, and infusion catheter 58 have been inserted into the vascular structure V, the wire guide 50 may be removed, as shown in FIG. 6. Next, the clot removal system 10 or, more specifically, the sheath 14 and catheter 30 may be moved from the transport configuration to the deployed configuration. In the deployed configuration, the distal segment 40 of the catheter 30 is advanced distally beyond the distal segment 44 of the sheath 14 and/or the sheath 14 is proximally withdrawn relative to the catheter 30. Specifically, according to the deployed configuration, one of the sheath 14 and catheter 30 is moved relative to the longitudinal axis $A_1$ such that the catheter segments 42 are no longer urged against the pre-shaped curved configurations by the lumen wall 46 of the sheath 14. Thus, according to the deployed configuration, the catheter wall segments 42 are able to conform to the pre-shaped curved configurations.

According to the embodiment of FIG. 2, and as shown in FIG. 6, the catheter wall segments 42 may include four leaflets 102 that radially expand and assume substantially concave, or scoop-like, shapes. Each of the leaflets 102 has a first directional cutting edge 104, a second directional cutting edge 106, and a soft distal tip 108. Alternatively, and according to the embodiments shown in FIGS. 3 and 7, the catheter wall segments 42 may include two leaflets 120 that are curved back over a portion of the catheter 30 and, in some cases, the sheath 14. Thus, transitioning to the deployed configuration may include moving the inner surface 47 of each wall segment 42 from a radially inward facing orientation to a radially outward facing orientation. Both of the leaflets 120 have first directional cutting edges 122, second directional cutting edges 124, and soft distal tips 126.

According to either embodiment described herein, or other similar embodiments, the catheter 30 may be axially reciprocated relative to and/or rotated about the longitudinal axis $A_1$ to break up, dislodge, or otherwise disrupt the clot 142. Specifically, for example, the catheter 30 may be rotated in a first direction about the axis $A_1$ such that the first directional cutting edges 104 or 122 engage the clot 142. Alternatively, or additionally, the catheter 30 may be rotated in a second, or opposite, direction about the axis $A_1$ such that the second directional cutting edges 106 or 124 engage the clot 142. The catheter 30 may be axially reciprocated before, during, and/or after the rotational movement, while the soft distal tips 108 or 126 reduce the likelihood of damaging the vessel wall 144.

Once a desirable portion of the clot 142 has been dislodged and/or dissolved, dislodged clot fragments may be removed, such as by aspiration, through the catheter 30 and/or sheath 14. Further, to remove the clot removal system 10 after the clot removal procedure is completed, the inflatable balloons 26 and 66 may be deflated. The infusion catheter 58 may be proximally withdrawn through the catheter 30, and the catheter 30 may be proximally withdrawn through the device lumen 18 of the sheath 14. Finally, the sheath 14 may then be proximally withdrawn from the vascular structure V.

It should be understood that the above description is intended for illustrative purposes only, and is not intended to limit the scope of the present disclosure in any way. Thus, those skilled in the art will appreciate that other aspects of the disclosure can be obtained from a study of the drawings, the disclosure and the appended claims.

What is claimed is:

1. A clot removal system, comprising:
an elongated tubular sheath; and
an elongated tubular catheter received within the sheath, wherein a distal segment of the catheter is split into a plurality of catheter wall segments, wherein each of the wall segments has a pre-shaped curved configuration and defines at least one scraping edge;
wherein the clot removal system has a transport configuration in which the distal segment of the catheter is axially aligned with a distal segment of the sheath and the wall segments are urged against the pre-shaped curved configuration by a lumen wall of the sheath, and a deployed configuration in which the distal segment of the catheter is advanced distally beyond the distal segment of the sheath and the wall segments conform to the pre-shaped curved configuration;
an elongated wire guide received within the catheter and having a distal segment extending beyond the distal segment of the catheter;
wherein a distal tip of each wall segment is less stiff than a remaining portion of the wall segment;
wherein the catheter is configured for rotation about a longitudinal axis; and
wherein the catheter has a tapered distal segment, and a portion of the distal segment is shaped as a dilator and protrudes distally beyond a distal end of the sheath in the transport configuration.

2. The clot removal system of claim 1, wherein, in the transport configuration, an inner surface of each wall segment faces radially inward and, in the deployed configuration, the inner surface of each wall segment faces radially outward.

3. The clot removal system of claim 1 wherein the catheter is plastic.

4. The clot removal system of claim 1, further including a inflatable balloon disposed on the distal segment of the sheath; and
the sheath has an inflation lumen that opens into the balloon.

5. A clot removal system, comprising:
an elongated tubular sheath; and
an elongated tubular catheter received within the sheath, wherein a distal segment of the catheter is split into a plurality of catheter wall segments, wherein each of the wall segments has a pre-shaped curved configuration and defines at least one scraping edge;
wherein the clot removal system has a transport configuration in which the distal segment of the catheter is axially aligned with a distal segment of the sheath and the wall segments are urged against the pre-shaped curved configuration by a lumen wall of the sheath, and a deployed configuration in which the distal segment of the catheter is advanced distally beyond the distal segment of the sheath and the wall segments conform to the pre-shaped curved configuration;
an elongated wire guide received within the catheter and having a distal segment extending beyond the distal segment of the catheter;
wherein a distal tip of each wall segment is less stiff than a remaining portion of the wall segment;
an infusion catheter having at least one distally disposed infusion port, wherein the infusion catheter is sized to be received within the catheter and sized to advance over the wire guide; and
the infusion port is positioned distally beyond the distal segment of the catheter in the deployed configuration.

6. The clot removal system of claim 5, further including a first inflatable balloon disposed on a distal end of one of the wire guide and the infusion catheter.

7. The clot removal system of claim 6, further including a second inflatable balloon disposed on the distal segment of the sheath.

8. A method for removing a clot from a patient vessel using a clot removal system, the clot removal system including an elongated tubular sheath, and an elongated tubular catheter received within the sheath, wherein a distal segment of the catheter is split into a plurality of catheter wall segments, wherein each of the wall segments has a pre-shaped curved configuration and defines at least one scraping edge, wherein the clot removal system has a transport configuration in which the distal segment of the catheter is axially aligned with the distal segment of the sheath and the wall segments are urged against the pre-shaped curved configuration by a lumen wall of the sheath, and a deployed configuration in which the distal segment of the catheter is advanced distally beyond the distal segment of the sheath and the wall segments conform to the pre-shaped curved configuration, and an elongated wire guide received within the catheter and having a distal segment extending beyond the distal segment of the catheter; wherein a distal tip of each wall segment is less stiff than a remaining portion of the wall segment; wherein the catheter is configured for rotation about a longitudinal axis; and wherein the catheter has a tapered distal segment, and a portion of the distal segment is shaped as a dilator and protrudes distally beyond a distal end of the sheath in the transport configuration, the method comprising steps of:
advancing the clot removal system through the patient vessel in the transport configuration toward the clot, wherein, in the transport configuration, the distal segment of the catheter is axially aligned with a distal segment of the sheath and the wall segments are urged against the pre-shaped curved configuration by the lumen wall of the sheath;
moving the clot removal system from the transport configuration to the deployed configuration, wherein, in the deployed configuration, the distal segment of the catheter is advanced distally beyond the distal segment of the sheath and the wall segments conform to the pre-shaped curved configuration; and
dislodging a portion of the clot from a vessel wall using the scraping edge of at least one of the wall segments.

9. The method of claim 8, further including rotating the catheter about a longitudinal axis.

10. The method of claim 8, further including axially reciprocating the catheter relative to the clot.

11. The method of claim 8, wherein the advancing step includes dilating the patient vessel with the tapered distal segment of the catheter.

12. The method of claim 11, wherein the moving step includes moving an inner surface of each wall segment from a radially inward facing orientation to a radially outward facing orientation.

13. The method of claim 11, further including advancing the wire guide through the patient vessel toward the clot and advancing the catheter and sheath over the wire guide.

14. The method of claim 13, further including:
advancing an infusion catheter over the wire guide and through the catheter; and
delivering a thrombolytic agent through at least one distally disposed infusion port of the infusion catheter and into the patient vessel.

15. The method of claim 14, further including distally deploying a first barrier relative to the clot by inflating a balloon disposed on a distal end of one of the wire guide and the infusion catheter.

16. The method of claim 15, further including proximally deploying a second barrier relative to the clot by inflating a second inflatable balloon disposed on the distal segment of the sheath.

17. The method of claim 16, further including:
proximally withdrawing the catheter from the sheath; and
aspirating portions of the clot through the sheath.

\* \* \* \* \*